United States Patent [19]
Guénin et al.

[11] Patent Number: 5,468,725
[45] Date of Patent: Nov. 21, 1995

[54] ALCOHOL FREE PERFUME

[75] Inventors: Eric P. Guénin, Piscataway; Karen A. Trotzinka, Wanamassa; Leslie C. Smith, Plainsboro; Craig B. Warren, Rumson, all of N.J.; Marina A. Munteanu, New York, N.Y.; Siew L. Chung, Old Bridge; Chee-Teck Tan, Middletown, both of N.J.

[73] Assignee: International Flvos & Fragrances Inc., New York, N.Y.

[21] Appl. No.: 253,315

[22] Filed: Jun. 3, 1994

Related U.S. Application Data

[63] Continuation-in-part of Ser. No. 130,179, Oct. 1, 1993, Pat. No. 5,320,863, which is a continuation of Ser. No. 84,610, Jul. 1, 1993, Pat. No. 5,283,056.

[51] Int. Cl.$^6$ ............................................ A61K 7/46
[52] U.S. Cl. .................................... 512/2; 512/3
[58] Field of Search ............................... 512/2, 3

[56] References Cited

U.S. PATENT DOCUMENTS

| | | | |
|---|---|---|---|
| 4,146,499 | 3/1979 | Rasano | 252/186 |
| 4,835,002 | 5/1989 | Wolf et al. | 426/590 |
| 5,045,337 | 9/1991 | El-Nokaly et al. | 426/602 |
| 5,079,227 | 1/1992 | Handjani et al. | 512/3 |
| 5,130,122 | 7/1992 | Tabibi et al. | 427/49 |
| 5,246,918 | 9/1993 | Behan et al. | 512/3 |

*Primary Examiner*—James H. Reamer
*Attorney, Agent, or Firm*—Arthur L. Liberman

[57] ABSTRACT

An alcohol-free transparent perfume is disclosed containing an alcohol-free perfume base, water and a stable transparent oil-in-water microemulsion flavor concentrate formed of water, at least one hydrophobic perfume oils, at least one cationic surfactant and at least one non-ionic surfactant in the absence of lower alkanols wherein the mixing ratio of water, oil and surfactant is defined according to the shaded area of FIG. 1.

6 Claims, 7 Drawing Sheets

5,468,725

ALCOHOL FREE PERFUME

REFERENCE TO A RELATED APPLICATION

This is a continuation-in-part of application Ser. No. 08/130,179 filed Oct. 1, 1993, now U.S. Pat. No. 5,320,863 which in turn, is a continuation of application Ser. No. 08/84,610 filed Jul. 1, 1993, now U.S. Pat. No. 5,283,056.

BACKGROUND OF THE INVENTION

The present invention relates to an alcohol free microemulsion, containing fragrance, and more especially to transparent oil in water microemulsion concentrates which consist essentially of water, one or more hydrophobic fragrance oils and one or more surface active agents. In another aspect, the present invention relates to a method for preparing transparent microemulsion perfume compositions.

Alcohol containing fragrances are the mostly commonly used vehicle in preparing fine perfumes. Alcohol has the advantage of being a material that has a fast evaporation rate and a strong lift of the fragrance after application to the skin. There is a worldwide incentive to reduce the use of volatile organic chemical (VOC). The replacement of alcohol base product by microemulsion based product is considered as a step in this direction. The market of alcohol free fragrances constitutes a new segment of activity which has an important growth potential in the future. Since this trend is recent, all the advantages of alcohol-free fragrances have yet to be discovered. In any case, the success of this product is based on the potential to harmonize the aroma chemical with the aqueous base. This involves the proper choice of aroma chemicals to generate a different olfactory experience, but also the proper choice of surfactant and surfactant concentration, to impart transparency and skin substantivity.

There is currently a movement in the perfume industry towards elimination of alcohol in fragrances and the development of water based fragrances and perfumes. These new formulations would have the advantage of eliminating the problems caused by volatile organic chemical restrictions imposed by various countries as well as objections from environmentalist groups and persons concerned with infant safety as well as objections to alcohol in some countries based on religious grounds. Hence there have been many efforts to utilize water as a solvent for perfumes.

Water as a solvent for perfumes does have problems because it has different characteristics and properties from alcohol in terms of solubilities, drying rates, odor and the like. As a result, efforts in the past to utilize water as a base for perfumes has not been met with great success.

One approach to prepare water based perfume formulations has resulted in the development of microemulsion technology which is capable of yielding a clear to opalescent, low viscosity solution.

The concept of the microemulsion was introduced by Schulman and Montague, Ann. New York Academy of Science, 1961, Volume 92, page 366. Becher, American Chemical Society Symposium Series 448, ACS, Washington, D.C. 1991 contains two chapters covering microemulsions in foods: Chapter 1, El-Nokaly, et al. and Chapter 2, Friberg, et al. The microemulsion system typically contains relatively large amounts of oil and water along with a surfactant and co-surfactant except in the case of certain hydrophobic surfactants where no co-surfactant may be required. These systems are indicated in the prior art to form spontaneously as a result of contact between the several components.

The most characteristic difference between an emulsion and a microemulsion is the appearance of the microemulsion and the emulsion. An emulsion is turbid while the microemulsion is transparent.

Rosano, U.S. Pat. No. 4,146,499 issued on Mar. 27, 1979 discloses a method for the preparation of oil-in-water microemulsions via a four-step process: 1) a surfactant is selected which is just barely soluble in the oil phase; 2) the surfactant thus selected is dissolved in the oil to be emulsified in an amount effective to yield a fine emulsion of the emulsified oil in an aqueous phase; 3) the oil, together with its dissolved surfactant is added to the water phase and shaken or stirred; and 4) finally there is provided a second surfactant in the water phase which is somewhat more soluble in water than the first surfactant to produce a substantially clear microemulsion of oil in water. Wolf, et al. U.S. Pat. No. 4,835,002 issued on May 30, 1989 discloses microemulsions of edible oils in a matrix of water and certain alcohols which are prepared using certain edible surfactants for use in various products such as beverages. El-Nokaly, et al. U.S. Pat. No. 5,045,337 issued on Sep. 3, 1991 discloses microemulsions which are thermodynamically stable, clear and homogeneous which are made from a polar solvent, a specific polyglycerol mono, diester and a lipid. El-Nokaly, et al. discloses that these microemulsions are edible, have good flavor and can be used to disperse water soluble nutrients, vitamins, flavors and flavor precursors in oils. The polyglycerol mono diester in El-Nokaly, et al. consists of a mixture of mono and diesters of branched or unsaturated fatty acids having from 12 to 24 carbon atoms and a polyglycerol mixture consisting of 0% to 10% monoglycerol and other polyglycerols, 30% of less diglycerol, 25% to 50 triglycerol, 15 to 50% tetraglycerol. Tabibi, et al. U.S. Pat. No. 5,130,122 issued on Jul. 14, 1992 discloses oral cavity and dental products prepared by microemulsifying an adsorptive oil in an aqueous medium to produce uniform submicron sized droplets. It is disclosed by Tabibi, et al. that the disclosed therein avoid the generally unaesthetic, oily, and unpleasant taste problems of previous similar products. For certain fragrances compositions known in the art, the combustion of a solubilizer which is a high HLB surfactant with a fragrance oil does not provide an adequate range of clear product.

SUMMARY OF THE INVENTION

It is an object of the present invention to provide an nonalcoholic fragrance formulation of improved properties and especially of decreased turbidity.

Another object of the present invention is to provide fragrance compositions containing little or no lower alkanols such as ethyl alcohol but which at the same time will maintain stability and yield transparent or essentially transparent product.

These and other objects of the present invention are accomplished by providing a selective composition comprising as the essential ingredients a fragrance, water, and a cationic and a non-ionic surface active agent. In addition to the essential ingredients the formulations of the present invention can contain other solubilizers, amphoteric surfactants, anti-foaming agents, anti-sticking agents preservatives and as well as conventional additives well known in the perfumery art which contribute their expected function to the ultimate products obtained herein.

A feature of the invention is in the use of a very small amount of cationic surfactant with an aqueous system of a fragrance oil and non-ionic surfactant to enhance the transparency of an alcohol free fragrance microemulsion.

BRIEF DESCRIPTION OF THE DRAWINGS

The present invention will be further understood with reference to the drawings wherein.

DETAILED DESCRIPTION OF INVENTION

Figure 1:
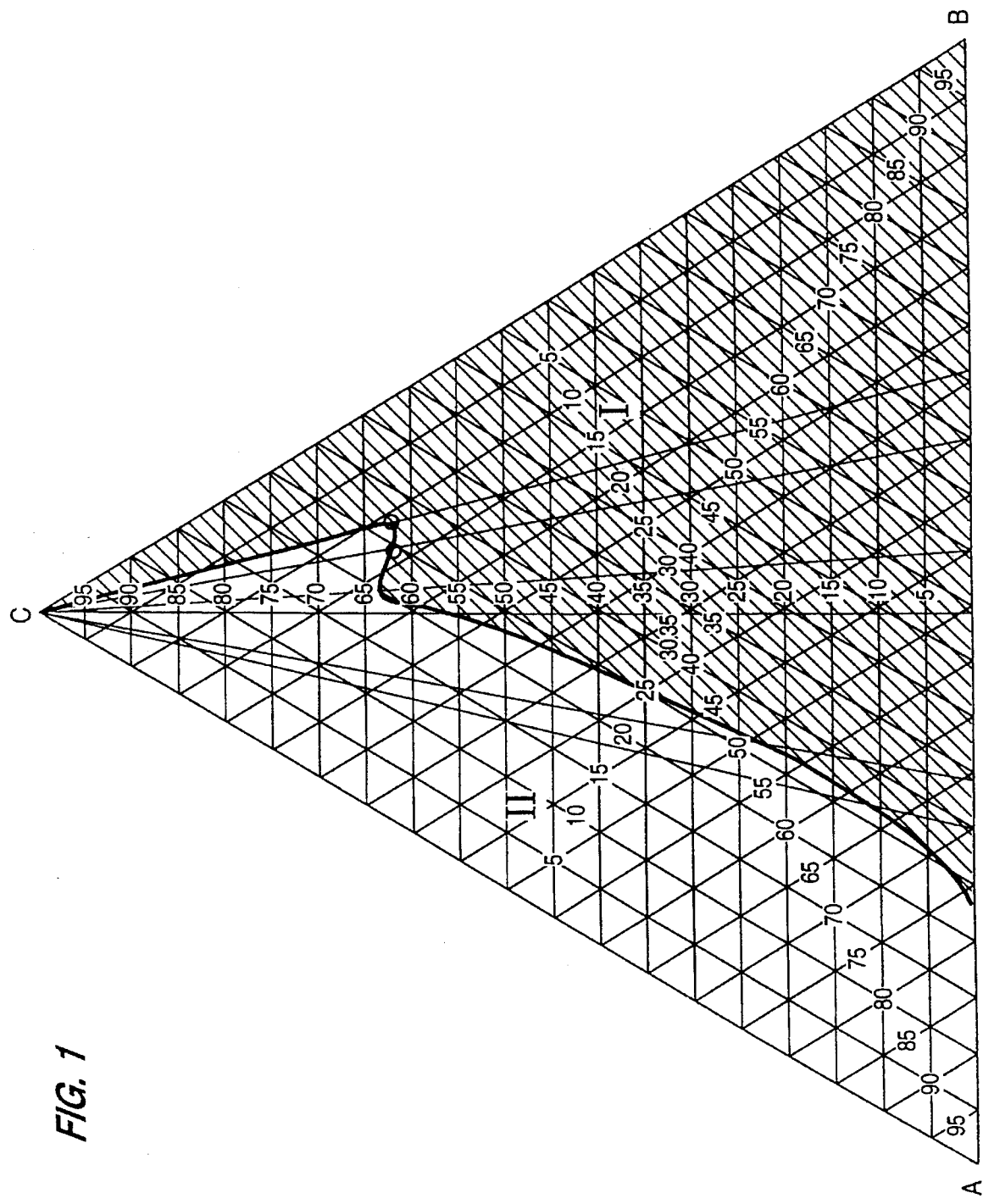
FIG. 1 is a ternary phase diagram of fragrance oil (Lillial), surfactant (Cremophor® RH60) and an aqueous solution of Luviquat® mono CP surfactant showing in the shaded area (I) the stable transparent microemulsion in accordance with the invention.

In carrying out the process of the invention, there is formed a stable oil in water microemulsion fragrance concentrate formed of water, one or more perfumes or aromatic chemicals and one or more cationic and non-ionic surfactants wherein the mixing ratio of oil, water and surfactants is as shown in the drawings. Referring to FIG. 1 the desired range is surrounded and defined by the lines connecting "A'" (almost 80% fragrance oil) point "B" (100% of surfactant) and "C" (100% water plus a small amount of cationic surfactant), excluding the points "A"', "B", and "C", the line connecting points "A'" and "B", the line connecting points "B" and "C" and the curve connecting points "A'" and "C" wherein all of said three components are present. The curve connecting points "A'" and "C" can be described by the mathematical model:

$$z = ax + \beta y + a'x^2 + \beta'y^2 + a''x^3 + \beta y''^2 + \gamma xy + \gamma'x^2y + \gamma''xy^2$$

wherein z is the percent fragrance oil; x is the percent water and y is the percent surfactant; and wherein the terms:

$\alpha$ $\alpha'$ $\alpha''$ $\beta$ $\beta'$ $\beta''$ $\gamma$ $\gamma'$ and $\gamma''$ are constants In general a combination of non-ionic and cationic or amphoteric surfactants is used. The fragrance and non-ionic solubilizer can be first mixed together and the cationic surfactant agent is added. Next the small amount of antifoaming agent and the distilled water solution is added according to the formula. The turbidity is determined in a standard way by measuring the visible light absorbance of individual solutions at 400 nm on a spectrophotometer. The control used is distilled water which is rated at 100% transmittance and zero absorbance.

The fragrance oil used in accordance with the present invention may be one or mixture of oils soluble in one another. Such perfume oils are well known and include for example lavender oil or any other suitable fragrance chemical. The fragrance oil selected herein for exemplification is but one of a wide variety.

The non-ionic surfactants used for in the practice of invention include all non-ionic surfactants known for use in perfumes. Examples of such surfactants are the following:

TWEEN® 20 (polyoxyethylene (20) Sorbitan Monolaurate)

TWEEN® (is a Trademark of ICI Americans of Wilmington, Del.

TWEEN® 40 (Polyoxyethylene (20) Sorbitan Monopalmitate);

TWEEN® 60 (Polyoxyethylene (20) Sorbitan Monosterate);

TWEEN® 80 (Polyoxyethylene (20) Sorbitan Monooleate);

CREMOPHOR® RH 40 (Ethoxy Hydrogenated Castor Oil) (CREMOPHOR® is a Trademark of BASF Aktiengesellschaft of D-6700 Ludwigshafen, Federal Republic of Germany);

CREMOPHOR® RH 60 (Ethoxy Hydrogenated Castor Oil);

GENAPOL® (Alcohol Polyglycol Ether) (GENAPOL® is a trademark of Hoechst Aktiengesellschaft of D-6230 Frankfurt AM Main No. 90, Postfach 80, Federal Republic of Germany);

Sodium Lauryl Sulphate;

POLOXAMER® 407 (also known as PLURONIC® F127) and PLURACARE® f1277 (ethylene oxide-propylene oxide block copolymer having an average molecular weight of 12,600) (POLOXAMER®, PLURONIC® and PLURACARE® are Trademarks of BASF Corporation of Parsippany, New Jersey 07054).

SPAN® 20 (Sorbitan Monolaurate) SPAN® is a trademark of ICI Americas of Wilmington, Del. 19897);

SPAN® 40 (Sorbitan Monopalmitate);

SPAN® 60 (Sorbitan Monostearate); and

SPAN® 80 (Sorbitan Monooleate).

The formula for the SPAN®s are well known in the art.

TWEEN®s are polyoxyethylene-substituted SPAN®s. Reference: The Merck Index, 8th Edition, Published by Merck & Company Inc. Rahway, N.J. 1968, at pages 848, 849 and 973.

The foregoing surfactants can be used taken alone or taken in combination of two or more.

The water phase can be pure water or may contain small amounts (e.g., less than 1%) of preservative, antimicrobial and humectant added when necessary. Such compounds are sodium benzoate, sodium or potassium propionate, potassium sorbate, glycerol and propylene glycol.

It is an essential feature of the invention that one or more cationic surfactants be present to enable the formation of a desired perfume formulation. The desired compositions of the present invention have low viscosity, low stickiness and low foaming. Antistick and anti-foaming agents are introduced into the formulation to contribute their expected functions.

Cationic surfactants are compatible with nonionic and amphoteric surfactants. As a rule, they cannot be used together with anionic surfactants because they interact to form water-insoluble salts (or complexes). Cationic surfacts are strongly adsorbed by negatively charge substrates, which include skin and hair, glass, ceramics, metallic oxides and clays, and most importantly many types of microorganism.

The following is a discussion of some well known types of cationic surfactants.

Long chain primary, secondary, and tertiary amine salts exhibit surface activity and find numerous industrial applications (ore flotation, corrosion inhibition in fuels and lubricants). On the other hand, quaternary ammonium salts are the major types of cationic surfactant used in cosmetics and toiletries.

Quaternary salts, normally in the form of their hydrochlorides or hydrobromides, are widely used in drugs and cosmetics in light of their antimicrobial properties and their substantivity to negatively charged surfaces. In contrast to primary, secondary, and tertiary amine nitrogens, the quaternary nitrogen atom retains its positive charge regardless of the pH of the medium. The most important members of this group are antimicrobials, which are characterized by possessing only one long chain alkyl group; those that contain more than one fatty group are more useful as fabric or hair conditioning agents.

Ethoxylation of a primary amine increases its water solubility and provides nitrogen derivatives that under certain pH conditions can carry a positive charge. Alkylation of such a tertiary nitrogen with an alkyl halide leads to water-soluble quaternary compounds that have application in the textile industry to reduce static charges and for dye leveling.

With regard to the cationion surfactants to be used in the formulation, in general long chain cationic surfactants, known as Luviquat, Mono-CP® is preferred. These are cetyldimethyl-2-hydroxyethylammonium dihydrogen phosphate:

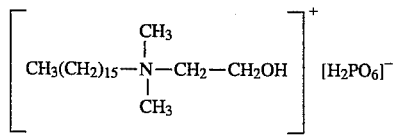

and related compounds:

Also are included among the suitable cationic surfactants are derivatives from phospholipids; e.g. Linoleamidopropyl phosphtidyl PG-Dimonium chloride Cocamidopropyl phosphotidyl PG-Dimonium chloride Stearaminopropyl phosphotidyl PG-Dimonium chloride Benzalkonium chloride The preferred cationic surfactants include, for example, the substances known as Luviquats®, especially FC grades. These are well known polyquaternary polymers based on a copolymer of vinylpyrrolidone and vinyl-imidazolium methachloride. A specific example is Luviquat® HM 552 and Luviquat® Mono CP of BASF. The latter is hydroxy ethyl cetyldimonium phosphide.

The cationic surfactant is added in an amount of 0.15% to 0.25% by weight of a 30% solids solution of the surfactant which is 0.045% to 0.075% by weight in water.

An amphoteric surfactant can also be used. These are made up of a number of zwitterionic specialty materials. They are commonly used in the skin and hair products as relatively mild detergents. They are not particularly useful as emulsifiers but show pH-dependent substantivity to substrates. At high pH values they behave as anionics; at intermediate pH they exhibit both anionic and cationic properties; finally, at low pH they perform as cationics.

Examples of amphoteric surfactants are the acrylic acid derivatives including the so-called alkylaminopropionic acids as well as alkyliminodipropionic acids. The former are synthesized by the addition of one molecule of a fatty alkyl amine to acrylic acid. If the alkylaminopropionic acid is reacted with a second molecule of acrylic acid, the so-called iminodipropionic acids result. Both of these materials are available as free acids or as salts.

Further examples are substituted alkylamides, N-alkyl betaines and phosphatides.

The microemulsion of our invention is prepared by following the shaded areas of the phase diagrams of FIGS. 1–7, inclusive using surfactant, fragrance oil and water as the components. The procedure is to mix fragrance oil first with surfactants; then add water. The resulting mixture is mixed for a short period of time (between from about 5 seconds up to about 10 minutes) depending on the property of the mixture. When the surfactant is in solid form or is highly viscous, the mixture is heated in order to ease the mixing. When a microemulsion is formed the mixture becomes transparent to white light.

The microemulsion of our invention preferably has a viscosity in the range of from about 1 up to about 18,000 centipoises at a temperature in the range of from 20° C. up to 30° C. and a refractive index in the range of from 1.4 up to 1.6 at a temperature in the range of from 20° C. up to 30° C. The perfume is present in the formulation from about 0.005% to about 20% by weight.

The stable transparent oil and water microemulsion fragrance concentrate of our invention consists essentially of:

(i) water (ii) one or more hydrophobic perfume oils; and (iii) one or more non-ionic surfactants and/or (iv) one or more cationic surfacts and/or (v) one or more amphoteric surfactants and/or zwitterionics substantially in the absence of lower alkanols such as ethanol. The mixing ratio of water, oil and surfactant is illustrated in the phase diagrams FIGS. 1–4. Thus, for to FIG. 1 the range is surrounded and defined by the lines connecting point "A" (almost 80% of fragrance oil), point "B" (100% surfactant) and point "C" (100% water plus cationic surfactant) excluding the points "A", "B" and "C", the line connecting points "A'" and "B" and the curve connecting points "A'" and "C" wherein all three components are present. The point indicated "C" 100% water. The point indicated "A" 100% fragrance oil. Point A' is not approximately 778% fragrance oil. The side of the diagram defined by line A-C shows increasing values from 0% oil up to 100% oil and decreasing values of water from 100% water down to 0% water. The side defined by the line C-B shows increasing amounts of surfactant from 0 to 100% starting from point C and ending at point B and decreasing amounts of water from 100% down to 0% from point B to point C.

Figure 2:
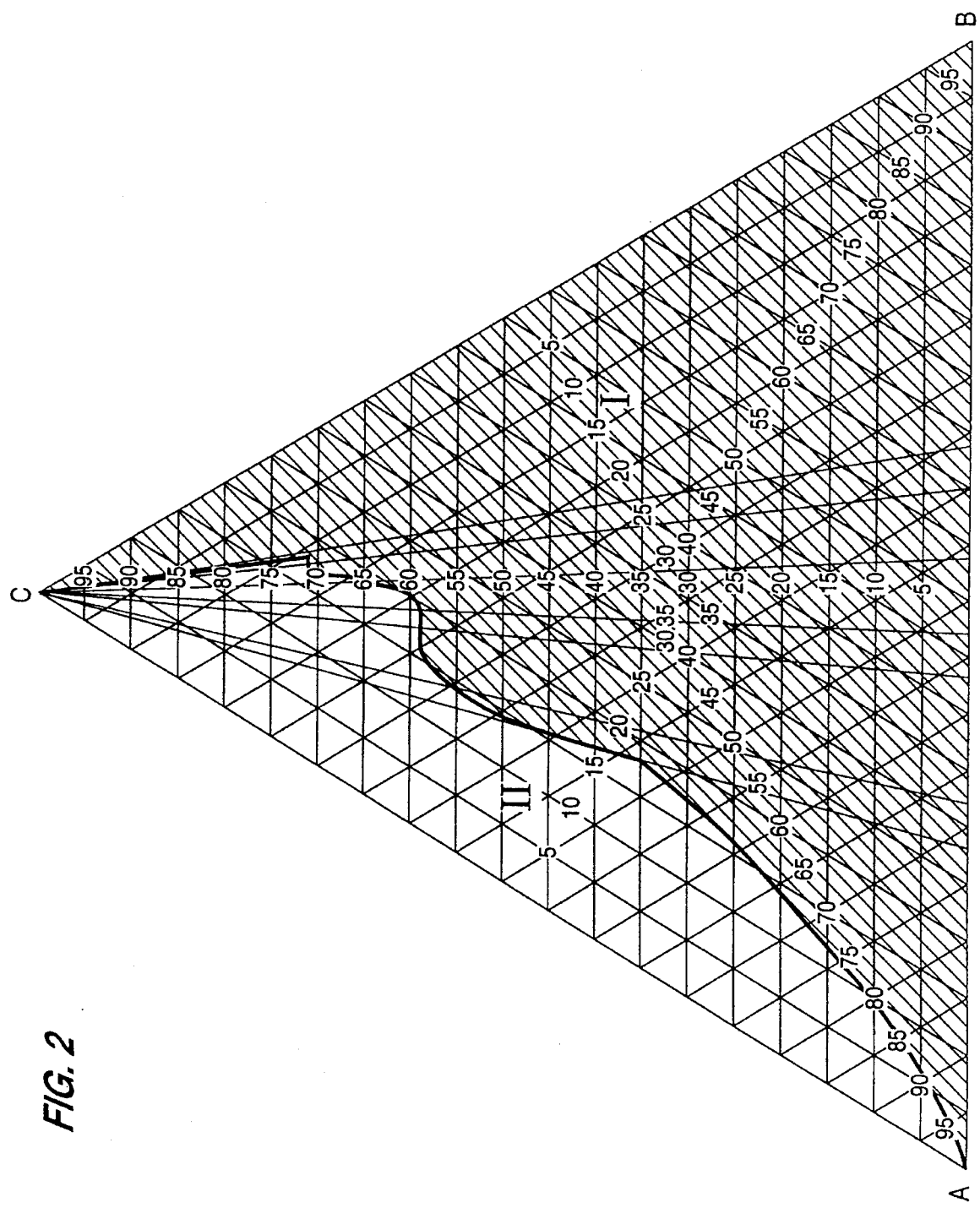
FIG. 2 is a ternary phase diagram of (a fragrance oil (Lillial), surfactant and water showing in the shaded area (I) the stable microemulsion in accordance with the invention.

Referring to FIG. 2, the ternary phase diagram shows a phase envelope bonded by the curve from point "C" to point "A" and by the lines "C"-"B" and "B"-"A". The shaded area indicates the microemulsion of the invention. One hundred percent fragrance oil is indicated by point A. One hundred percent water is indicated by point C. One hundred percent surfactant is indicated by point B.

Figure 3:
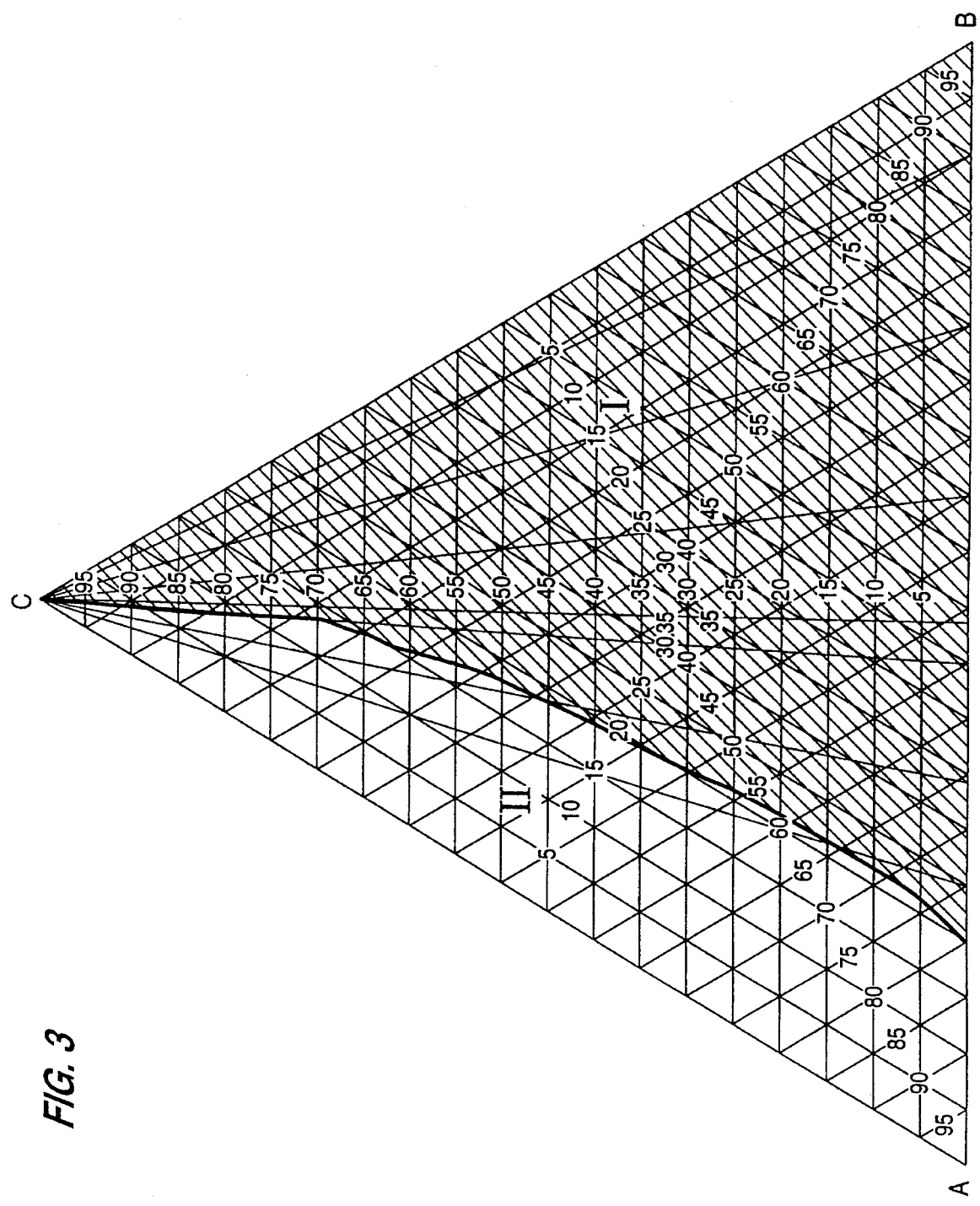
FIG. 3 is a ternary phase diagram of the fragrance oil (Lillial), LRI® surfactant and an aqueous solution of Luviquat® surfactant showing the stable microemulsion in the shaded area (I) according to the invention.

FIG. 3 is a ternary phase diagram of a specific system of the transparent microemulsion of the invention which is a stable transparent oil-in-water microemulsion perfume consisting essentially of:

(i) water and 0.15% Luviquat® mono CP (30% solid in water);

(ii) Lillial perfume oil; and (iii) LRI non-ionic surfactant mixture in the absence of lower alkanols.

The shaded area of the diagram indicates the stable transparent oil-in-water microemulsion perfume concentrate area. Point A indicates 100% perfume oil (Lillial). Point B indicates 100% detergent LRI consisting of CREMOPHOR® RH 40; and PPG 226 Buteth 226.

Figure 4:
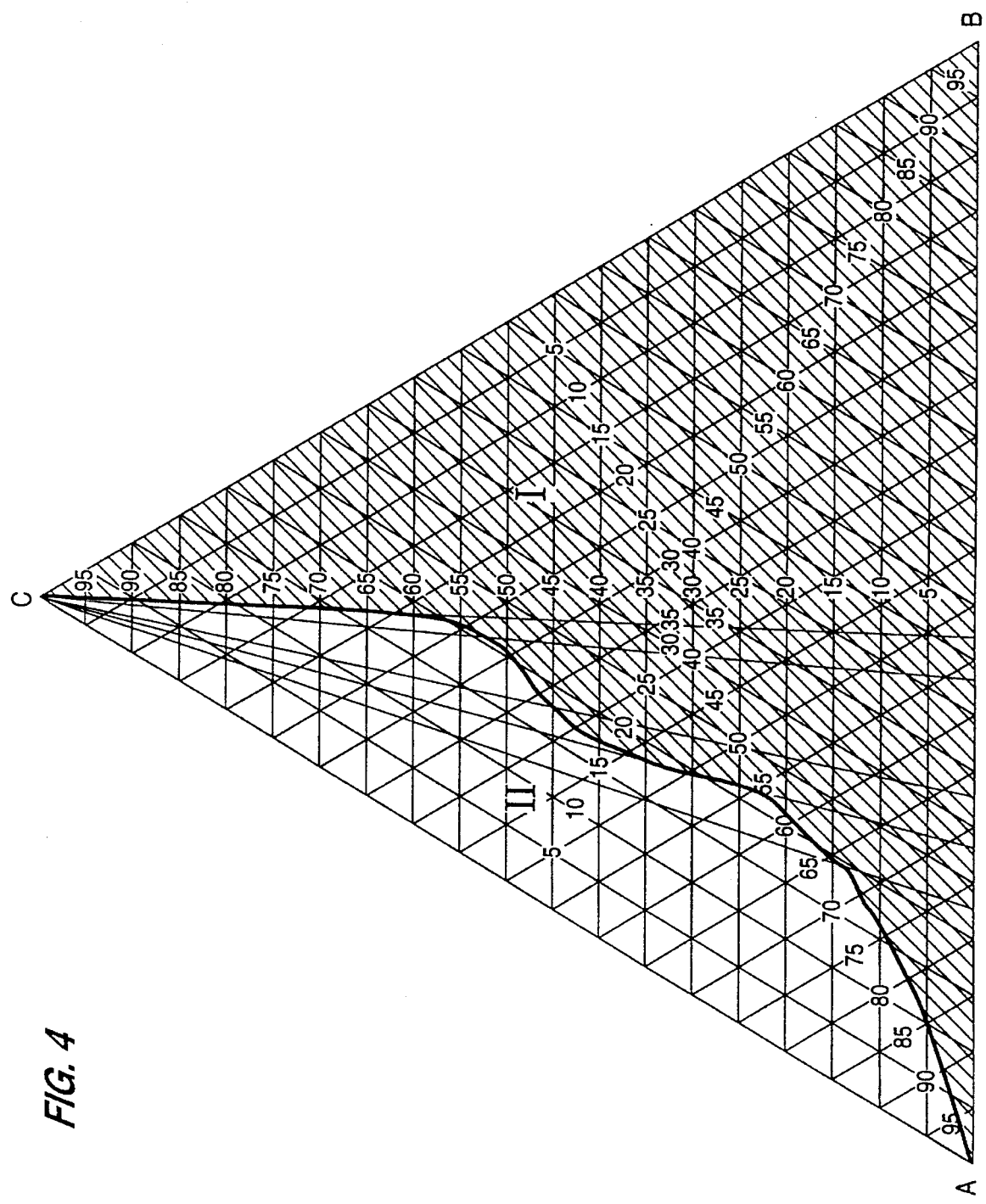
FIG. 4 is a ternary phase diagram of a fragrance oil (Lillial), LRI® surfactant and water showing the stable microemulsion in the shaded area (I) the according to the invention.

FIG. 4 is another ternary phase diagram which covers stable transparent oil-in-water microemulsion flavor concentrates consisting essentially of:

(i) water;

(ii) a hydrophobic perfume oil (Lillial); and (iii) LRI surfactant.

The shaded area region I is the area of the phase diagram covering the microemulsifion components of the invention. Point B indicates 100% detergent, point C indicates 100% water and point A indicates 100% perfume oil.

The 2-phase diagrams in FIGS. 1–4 are of the "before" and "after" type and show the change in turbidity with and without cationic surfactant.

Figure 5:
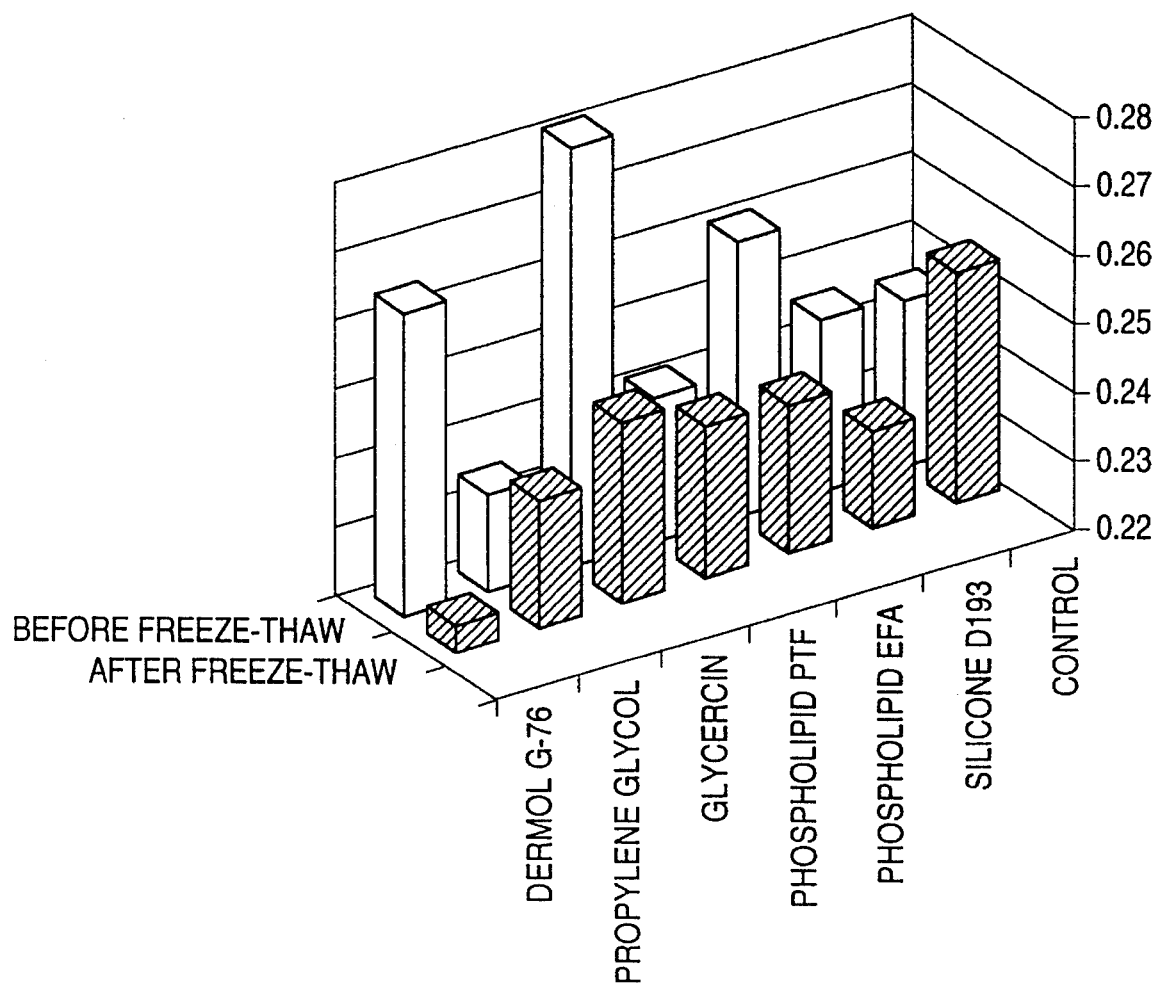
FIG. 5 is a bar graph showing turbidity as measured by absorbance of various components of skin conditioner formulations using alcohol free perfumes.

FIG. 5 is a perspective view of a bar chart showing the results of testing of conventional additives used in the skin care field on the adsorbance of light by the materials compared to a control which is distilled water.

Figure 6:
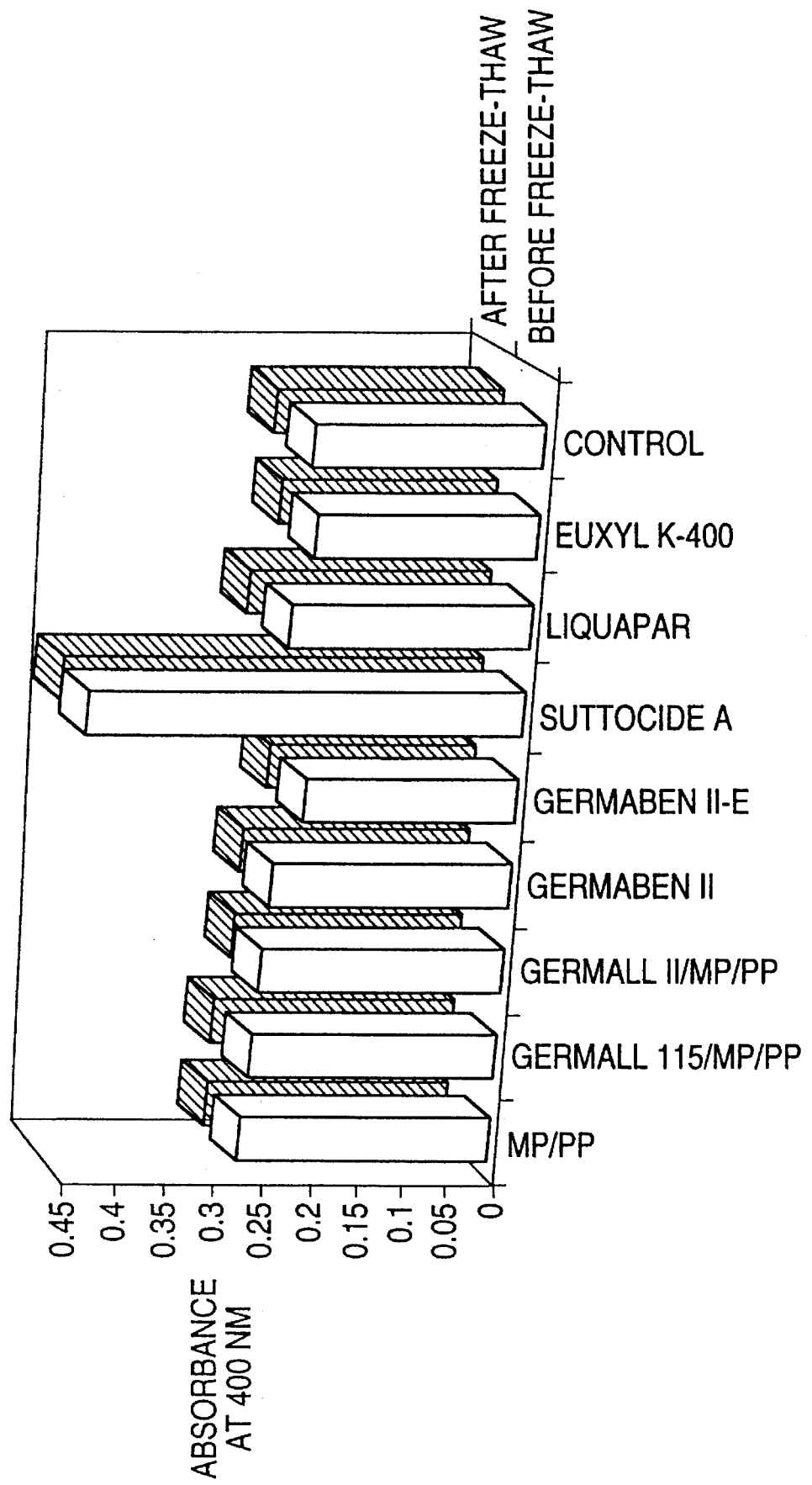
FIG. 6 is a bar graph showing preservative effect on turbidity.

FIG. 6 is a perspective view of a bar graph showing the effect on turbidity of various conventional preservatives before freeze-thaw and after freeze-thaw compared to a control of distilled water.

Figure 7:
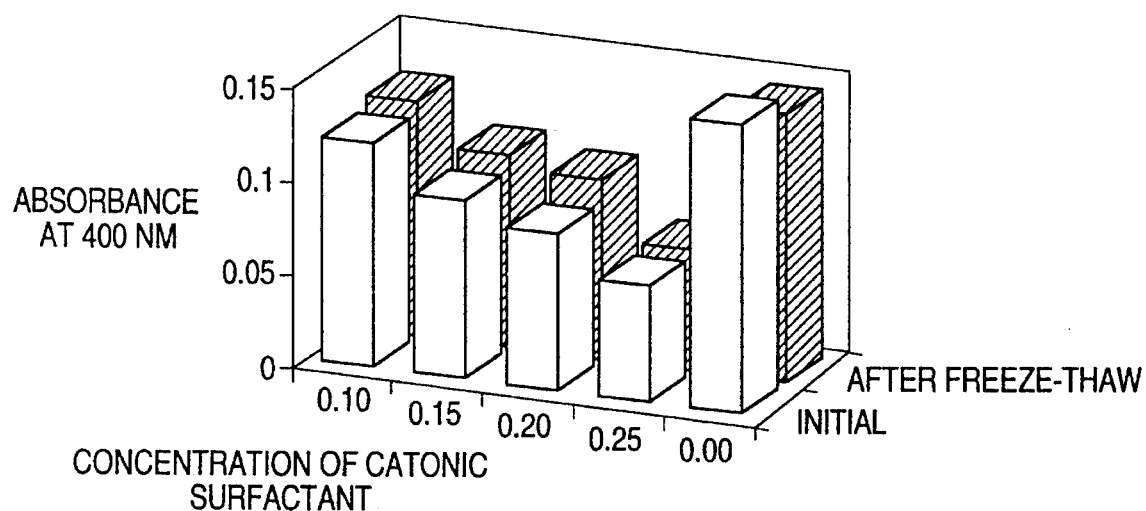
FIG. 7 is a bar graph showing the effect of a cationic surfactant on turbidity.

FIG. 7 is a bar graph showing the effect of amount of cationic surfactant on turbidity measuring absorbency with 6% of the non-ionic surfactant.

Figure 8:
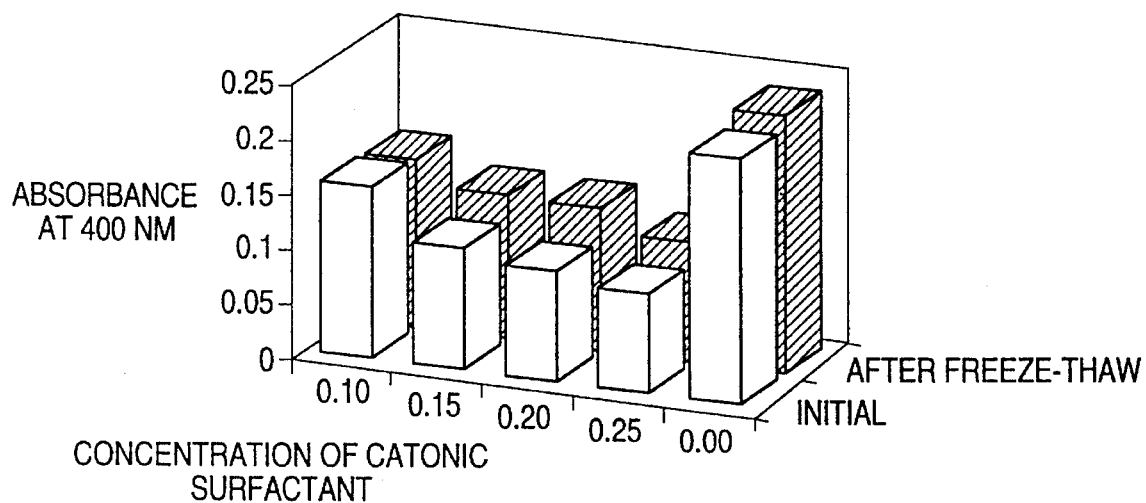
FIG. 8 is a bar graph showing effect of a cationic surfactant on turbidity.

FIG. 8 is another bar graph similar to FIG. 7 but with only 5% of the non-ionic surfactant.

The following examples were prepared with the following formulations:

A non-ionic surfactant compound of:

CREMOPHOR® RH 40

PPG 26 Buteth 26

Hydroxyethyl cetyl ammonium phosphate

Polypropylene glycol

Fragrance

Preservative (Paraben)

The formulations were evaluated as an alcohol free aftershave, an alcohol free cologne, an alcohol free baby cologne and an alcohol free water based sprayable air freshener or deodorant.

The following fragrances were prepared:

| I | |
|---|---|
| Sacramento fragrance | 2 grams |
| Cremophor® RH 40 | 5 grams |
| Luviquat® Surfactant | 0.2 grams |

-continued

| | |
|---|---|
| Water | to 100 grams |
| II | |
| Desert Sun | 2 grams |
| Cremophor® RH 40 | 5 grams |
| Luviquat® Surfactant | 0.2 grams |
| Water | to 100 grams |

Based on the work that was done in connection with this invention, the following formulation types are noted:

| Non-ionic surfactant | |
|---|---|
| Solubilisant (LRI) | 0.5–10% |
| (Cremophor® RH 40) | 0.5–10% |
| and | |
| (PPG 26 Buteth 26) | 0.5–10% |
| Cationic Surfactant B (LUVIQUAT®) | 0.2–4% |
| (30% invention) | |
| Antifoam agent | 0.002–0.008% |
| Preservative | 0.1–0.5% |
| Fragrance | 0.05–3% |
| Balance water | |

In accordance with the invention it was found that the combination of fragrance compounds with a high concentration of terpene aroma chemicals was improved by the addition of small amounts of cationic surfactant. Very small amounts of cationic surfactants turbidity of the system.

In a further effort to determine the effect of cationic surfactant concentration on turbidity of a insect repellent fragrance alcohol free microemulsion, the following work was done.

Solubilizer in the form of a non-ionic surfactant (LRI), fragrance oil, antifoam agent, prefervative, cationic surfactant (Luviquat®).

The fragrance and the solubilizer are first mixed together, then the cationic surfactant is added. Next the 0.002% antifoam-distilled water solution is added according to the formula. The turbidity was determined by measuring the absorbance of individual solutions at 400 nm on a spectrophotmeter.

A physical observation of the samples demonstrated improvements in the appearance of the microemulsion. The turbidity study (Table 1) shows that the addition of small quantity of the cationic surfactant decreased the turbidity of half its value. This represents a 100% improvement over the simple solubilizer mixture. This results is dramatic because of the nature of the fragrance. A fragrance with less terpene and geraniols would require a different approach.

TABLE 1

| Sample # | LRI % | Cationic Surfactant % | Turbidity (400 NM) Initial | Turbidity (400 NM) After Freeze/Thaw |
|---|---|---|---|---|
| 1 | 6 | 0.10 | 0.119 | 0.122 |
| 2 | 6 | 0.15 | 0.095 | 0.101 |
| 3 | 6 | 0.20 | 0.081 | 0.087 |
| 4 | 6 | 0.25 | 0.061 | 0.061 |
| 5 | 6 | 0.00 | 0.143 | 0.134 |
| 6 | 5 | 0.10 | 0.156 | 0.151 |
| 7 | 5 | 0.15 | 0.113 | 0.130 |
| 8 | 5 | 0.20 | 0.101 | 0.123 |
| 9 | 5 | 0.25 | 0.090 | 0.100 |
| 10 | 5 | 0.00 | 0.211 | 0.215 |

LRI is a 50:50 mixture of cremophor RH 40® and PPG 26 Beteth 26®.

Further variations and modifications of the foregoing will be apparent to those skilled in the art and are intended to be encompassed by the claims appended hereto.

We claim:

1. An alcohol-free transparent perfume consisting essentially of an alcohol-free perfume base, water and a stable transparent oil-in-water microemulsion fragrance concentrate consisting of:

(i) water;
   (ii) at least one hydrophobic perfume oil;
   (iii) at least one cationic surfactant; and
   (iv) at least one non-ionic surfactant, in the absence of lower alkanols wherein the mixing ratio of water, oil and surfactant is defined according to the shaded area of FIG. 1 and wherein the transparent microemulsion perfume has a viscosity in the range of from about 1 up to about 18,000 centipoises at a temperature in the range of from about 20° C. up to 30° C.; and a refractive index in the range of from 1.4 up to 1.6 at a temperature in the range of from 20° C. up to 30° C.

2. The alcohol-free perfume of claim 1 wherein the transparent microemulsion is defined according to the shaded area of FIG. 2.

3. The alcohol-free perfume of claim 1 wherein the transparent microemulsion is defined according to the shaded area of FIG. 3.

4. The alcohol-free perfume of claim 1 wherein the transparent microemulsion perfume is defined according to the shaded area of FIG. 4.

5. The alcohol-free perfume according to claim 1 which additionally contains an anti-stick agent.

6. The alcohol-free perfume according to claim 1 which additionally contains an anti-foaming agent.

* * * * *